United States Patent
Berstis et al.

(10) Patent No.: US 7,093,479 B2
(45) Date of Patent: Aug. 22, 2006

(54) METHOD AND APPARATUS FOR INDICATING A PARAMETER OF TRANSMITTED FLUID

(75) Inventors: Viktors Berstis, Austin, TX (US); Michael P. Carlson, Austin, TX (US); Yen-Fu Chen, Austin, TX (US); John W. Dunsmoir, Round Rock, TX (US); Randolph M. Forlenza, Austin, TX (US); John P. Kaemmerer, Pflugerville, TX (US); Francis X. Kinstler, Cedar Park, TX (US); Sheryl S. Kinstler, Cedar Park, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/034,554

(22) Filed: Jan. 13, 2005

(65) Prior Publication Data

US 2006/0150712 A1 Jul. 13, 2006

(51) Int. Cl.
*G01N 33/00* (2006.01)

(52) U.S. Cl. ..................................... 73/23.2

(58) Field of Classification Search ............... 73/23.2, 73/31.05; 96/109, 110, 111, 112, 113, 117; 340/632, 633, 634
See application file for complete search history.

(56) References Cited

U.S. PATENT DOCUMENTS

| | | | | | |
|---|---|---|---|---|---|
| 5,060,506 | A | * | 10/1991 | Douglas | 73/24.01 |
| 5,065,691 | A | * | 11/1991 | Brighton | 116/274 |
| H1039 | H | * | 4/1992 | Tripp, Jr. et al. | 99/530 |
| 5,282,464 | A | * | 2/1994 | Brain | 128/207.15 |
| 5,539,624 | A | * | 7/1996 | Dougherty | 362/556 |
| 6,569,089 | B1 | * | 5/2003 | Covington et al. | 600/199 |
| 6,651,653 | B1 | * | 11/2003 | Honkonen et al. | 128/201.21 |
| 2002/0062681 | A1 | * | 5/2002 | Livingston | 73/24.01 |
| 2003/0189492 | A1 | * | 10/2003 | Harvie | 340/573.1 |

OTHER PUBLICATIONS

"Oxygen Concentrators," via Internet at www.portablenebs.com/concentrator.htm, ©2000-2001, printed Sep. 10, 2004.

* cited by examiner

*Primary Examiner*—Charles Garber
(74) *Attorney, Agent, or Firm*—E. E. Jack Richards, II; Winstead Sechrest & Minick, P.C.; Casimer K. Salys (57) ABSTRACT

The invention concerns a method and apparatus for indicating a parameter of a transmitted fluid. One embodiment of the invention comprises a fluid source operatively coupled to a conduit for transmitting a fluid from the fluid source. In addition, a sensor detects a parameter of the fluid, such as the percent oxygen content of the fluid. In response to the sensor detecting the parameter of the fluid, an indicator illuminates a portion of the conduit if a predetermined condition, such as a minimum percent oxygen content of the fluid, is satisfied.

20 Claims, 8 Drawing Sheets

METHOD AND APPARATUS FOR INDICATING A PARAMETER OF TRANSMITTED FLUID

BACKGROUND INFORMATION

1. Technical Field

The present invention relates to apparatuses and methods for indicating failure or satisfaction of a parameter of a fluid that is transferred through a conduit.

2. Description of the Related Art

Many people use breathing therapy, such as oxygen therapy, for various ailments such as asthma, emphysema, chronic bronchitis, occupational lung disease, lung cancer, cystic fibrosis and congestive heart failure. Many such diseases are chronic in nature and require long-term treatment regimens. Home-based oxygen therapy permits these individuals to lead active, productive lives by letting them receive oxygen therapy at home instead of in a hospital or doctor's office.

Home-based oxygen therapy is certainly liberating to those who require it. However, it presents a host of problems. First, a physician typically writes a prescription for oxygen therapy. The prescription dictates the flow rate in terms of liters of oxygen per minute (LPM or L/M) and how often the breathing treatment should be administered. Furthermore, sometimes the oxygen therapy must be administered while exercising, sleeping or sometimes continuously. A problem arises in that complicated equipment may be needed. Small liquid crystal displays or hard-to-read mechanical gauges are needed to display, for example, flow rate. Reading such devices while exercising or while reclining in a darkened room can be difficult. Furthermore, many patients may be elderly and may have failing eyesight. For this group of patients, reading parameters, such as the flow rate, is especially difficult. Therefore, an easier method for determining characteristics of a fluid, such as flow rate, is needed.

Before describing the potential solutions to this problem, further background regarding breathing treatments will be addressed. For instance, there are three common tools used for providing oxygen therapy: compressed gas, liquid gas or an oxygen concentrator.

First, with compressed gas, oxygen is stored, under pressure, in a cylinder equipped with a regulator that controls the flow rate. Because the flow of oxygen out of the cylinder is constant, an oxygen-conserving device may be attached to the system to avoid waste. This device releases the gas only when a patient inhales and stops the gas supply when the patient exhales. Oxygen can be provided in a small cylinder that can be carried with the patient as large tanks are heavy and are only suitable for stationary use.

Second, regarding liquid oxygen, oxygen is stored as a very cold liquid in a vessel very similar to a thermos. When released, the liquid converts to a gas that a patient may breathe. This storage method takes up less space than the compressed gas cylinder, and the patient may transfer the liquid to a small, portable vessel at home. Liquid oxygen is more expensive than the compressed gas. An oxygen conserving device may be built into the vessel to conserve oxygen.

Third, oxygen concentrators are electrically powered devices that separate oxygen from ambient air, concentrate the oxygen and then store the oxygen. This system does not have to be resupplied, as is the case with compressed gas, and it is not as costly as liquid oxygen. Small, portable systems have been developed that afford even greater mobility. However, compressed oxygen is needed as a backup in the event of a power failure.

Regardless of how the oxygen is stored or supplied, there are three common means for supplying oxygen from the fluid supply to the patient. A nasal cannula is a two-pronged device inserted in the nostrils. The cannula is connected to tubing carrying the oxygen. People who need a high flow of oxygen generally use a mask. Some people who use a nasal cannula during the day prefer a mask at night or when their breathing passages are irritated or congested. Transtracheal oxygen therapy requires the insertion of a small flexible catheter in the trachea or windpipe. The transtracheal catheter is held in place by a necklace. Since transtracheal oxygen bypasses the mouth, nose, and throat, a humidifier is required at flow rates of 1 LPM or greater.

While there are many ways to store the gas and to deliver the gas to the patient, all of the methods face the same limitations. As stated above, the methods use difficult-to-read electronic and mechanical gauges to indicate parameters such as flow rate, percent oxygen delivered and humidity. Therefore, an easier method for quickly and easily determining characteristics or parameters of fluid flow is needed.

SUMMARY DESCRIPTION

One embodiment of the invention entails an apparatus for indicating a parameter of fluid that is transferred in a conduit. A fluid supply delivers a fluid to a fluid conduit having an input and an output. A sensor may sense the fluid to detect a parameter of the fluid. A parameter may entail, for example, the oxygen concentration, flow rate, pressure, humidity, and/or temperature of the fluid. In response to the sensor detecting the parameter of the fluid, an indicator may indicate whether a first predetermined condition is or is not satisfied. For example, a predetermined condition may be that the fluid must be comprised of 80 percent oxygen. If the fluid comprises, for example, only 50 percent oxygen, the indicator may indicate the predetermined condition is not satisfied. In one embodiment of the invention, the indicator is a light source, such as a light emitting diode (LED). In the present example, detection of only a 50 percent oxygen content may result in the LED indicator being ignited. The LED may then illuminate a portion of the conduit. The LED may be positioned inside or outside the conduit and may illuminate the conduit from inside or outside the conduit. In another embodiment of the invention, the indicator may entail a fiber optic system or audio alarm.

In certain embodiments of the invention, the conduit may be constructed from a substantially translucent material. Thus, illumination of the LED, or fiber optic system, may illuminate a portion of the conduit from within the conduit, within the conduit walls or across the conduit walls. Thus, in keeping with the above example, a patient will quickly realize whether the desired 80 percent oxygen is present because the conduit may be illuminated in a certain color of light.

In another embodiment of the invention, the indicator may be activated in response to a second parameter, such as humidity of the gas, satisfying, or failing to satisfy, a preset condition or limit for the second parameter.

In another embodiment of the invention, a second indicator may be utilized, in further response to the first sensor detecting the parameter of the fluid, to indicate whether a first predetermined condition is satisfied. Thus, using the above example, if the fluid oxygen level is more than 80 percent, a second indicator, such as a second LED which is a different color than the first LED, may illuminate.

In yet another embodiment of the invention, the second indicator may indicate whether a second predetermined condition is satisfied. For example, the second LED may illuminate if the fluid has 85% humidity, which is higher than a predetermined humidity level such as 70% humidity.

In another embodiment of the invention, a fluid indicator device may be operatively coupled between a fluid source and a conduit. A sensor may be mounted to the fluid indicator device wherein the sensor may detect a first parameter of the fluid such as oxygen content. A first indicator, such as a LED, may also be mounted to the fluid indicator device. In response to the sensor detecting the oxygen content of the fluid, the LED may illuminate provided, for example, the oxygen content is too low. By doing so, the LED may project light into the conduit thus illuminating a portion of the conduit.

In another embodiment of the invention, a fluid conduit connects to a gas mask which is affixed to the head of a patient. A second sensor detects the proximity of the conduit output to a patient's body. The second sensor may be a thermistor which detects heat from the patient's body. The thermistor sense signal may be transmitted to an indicator such as an LED. Thus, if a second sensor detects that a first predetermined condition, such as certain temperature from the patient's body heat, is satisfied, the indicator may illuminate.

Another embodiment of the invention illustrates an alternative method for detecting proximity of the conduit to the patient. A sensor may incorporate technology such as a radiofrequency identification unit (RFID). The RFID is coupled to a transmitter antenna, which may be located near the mask and conduit. The transmitter antenna may subject the RFID to a specific frequency, provided the RFID is in sufficient proximity to the transmitter. The response from the RFID is then picked up by the receiver antenna. If the RFID response matches a characteristic frequency, the determination may be made by computer programming that the indicator may be illuminated.

Still another alternative embodiment of the invention comprises a fluid source that is operatively coupled to a conduit. The conduit may have a channel for an indicator such as an LED and fiber optic cable. If the conduit were to be crimped or kinked, the fiber optic cable would stop transmitting light at the sight of the kink. Thus, the indicator would indicate the location of resistance to fluid flow, due to the kink, within the conduit.

In yet another embodiment of the invention, a fluid source is operatively coupled to a conduit. The conduit may have another channel comprising a transmitter and fiber optic cable. The invention may also comprise a fiber optic relay system comprising an optical receiver. The receiver, upon receiving light from the transmitter, may deem such a receipt as a predetermined condition being satisfied. However, should a kink be placed in the conduit, the receiver would no longer receive light from the transmitter. Upon such a condition, the receiver may signal to a computing system that the conduit flow path has likely been compromised. An audio alarm may then be sounded.

In another embodiment of the invention, the aforementioned indicator comprises a vibrator device that vibrates the conduit when a predetermined condition, such as a minimum oxygen content, is not satisfied. The vibrating conduit would alert the patient to the oxygen content problem.

In other embodiments of the invention, instead of transmitting a therapeutic gas, such as oxygen, to a patient, the conduit fluid channel may transmit a fluid, in the liquid state, such as a medication in an intravenous (IV) drip system. Blood, with both liquid and solid components, may also be transmitted through the conduit fluid channel. Also, gasoline or other fluids, liquid, gaseous or a combination thereof, may be transmitted over long distances using the invention. For especially long transmissions wherein fiber optic systems are used as an indicator, a laser may be substituted for the LED light source. Furthermore, optical regenerators may be used to combat signal degradation.

The foregoing has outlined rather broadly the features of the present invention in order that the detailed description of the invention that follows may be better understood. Additional features and advantages of the invention will be described hereinafter, which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

Figure 1:
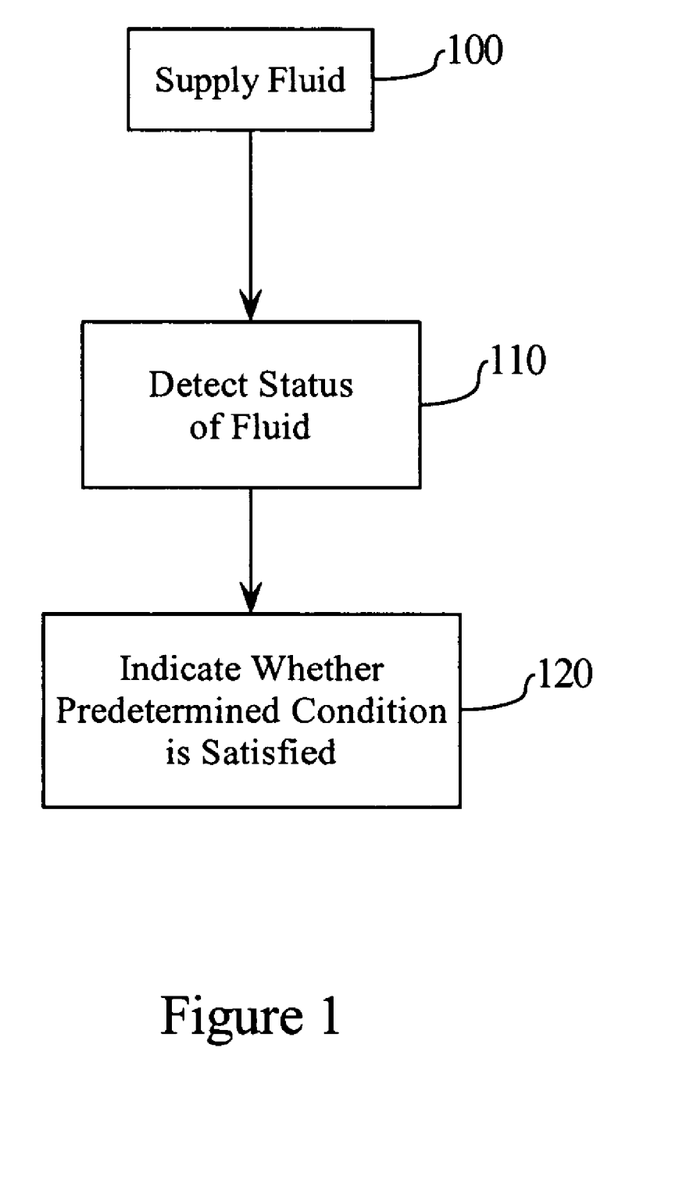
FIG. 1 is a flow diagram illustrating a method for indicating the parameter of fluid that is transferred in one embodiment of the invention.

FIG. 1 is a flow diagram illustrating a method for indicating the parameter of fluid that is transferred in one embodiment of the invention. The fluid may exist in a gaseous or liquid state, a combination thereof, or any of the preceding possibilities coupled with solid components mixed therein. One embodiment of the invention concerns a medical gas supply system. In step 100, a fluid is supplied from a fluid source. This fluid may be, for example, oxygen. In many medical regimens, a patient may need to take breathing treatments wherein the patient or subject should breath a gas mixture comprising at least, for example, 80 percent oxygen. In step 110, the fluid is analyzed. For example, the fluid may be analyzed to determine whether the fluid is comprised of at least 80 percent oxygen. Then, in step 120, if, for example, the fluid is not comprised of at least 80 percent oxygen, an indicator such as an audio or visual alarm may be initiated.

Figure 2:
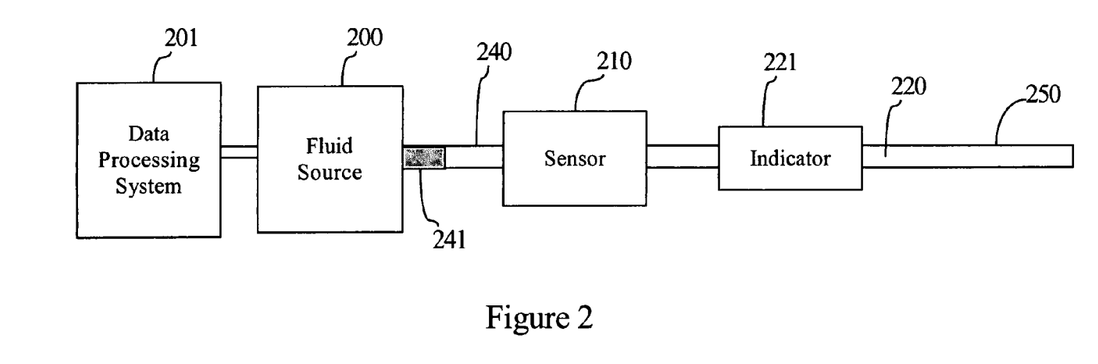
FIG. 2 is an apparatus for indicating the parameter of fluid that is transferred in one embodiment of the invention.

FIG. 2 illustrates an apparatus for indicating a parameter of fluid that is transferred in one embodiment of the invention. Keeping with the above example concerning a medical gas supply system, the fluid source 200 may take any of several forms. For example, the fluid source 200 may be a tank of compressed oxygen or mixture of different gases. The fluid supply may instead entail an oxygen concentrator. Suitable concentrators include the Airsep Newlife Elite model which produces ½ to 5 liters per minute of therapeutic oxygen.

The fluid may progress from the fluid supply or source 200 to a fluid conduit 220, also referred to herein as the conduit 220. A first sensor 210 may be in operative communication with the fluid that is transmitted through the conduit 220. This first sensor 210 may, acting independently or, for example, in concert with a data processing system 201, detect a parameter of the fluid. For example, the first sensor 210 may detect the oxygen concentration of the fluid. A person of ordinary skill in the art will appreciate that any number of electronic oxygen sensors are available and suitable for sensing oxygen levels of the fluid. For example, the Ultra Fast Oxygen sensor (UFO-130-2), by Teledyne Analytical Instruments, may suffice. A person of ordinary skill in the art will further appreciate that the sensor need not necessarily be physically immersed in the fluid. For example, infrared and acoustic technologies are available for sampling parameters of fluids without the sensor necessarily being immersed in the fluid.

In another embodiment of the invention, the first sensor 210 may comprise a flow sensor which may be used to determine fluid flow. A person of ordinary skill in the art will appreciate that such devices are readily available. Such sensors may require that the sensor be in communication with the fluid. Flow sensors can be used to measure gas or liquid flow or flow of mixed phases such as steam.

The flow sensor may comprise a number of different sensors, including differential pressure meters, velocity meters and true mass meters. These sensors can display flow values in a number of different ways. Volumetric flow rate shows how much of the measured medium passes through the sensor. Velocity flow rate shows the speed of the medium. Mass flow rate shows the weight or mass of the medium and might be displayed in units of pounds per minute or a similar unit. With many mass flow rate sensors, the sensor's output is based on the difference between two temperature sensors, one on each side of a heater (upstream and downstream). Thus, first sensor 210 may comprise a temperature sensor that is independent or coupled to the flow sensor. Regarding mass flow rate sensors, the heater and sensors consist of a thin film of platinum deposited between two layers of silicon nitride passivation. Holes are cut through the passivation and silicon is anisotropically etched from under the silicon nitride to form two bridges. Each bridge includes one temperature sensor and ½ of the heater. Flow sensors such as the 600 Series Accu-Flow™ (600HVACL04CON), by Sierra Instruments, or the AWM720P1 microbridge mass air flow sensor, by Honeywell, are some of the many options that will suffice.

In yet another embodiment of the invention, the first sensor 210 may sense humidity. Such a sensor may contain a laser-trimmed, thermoset polymer capacitive sensing element with integrated on-chip signal conditioning on a silicon substrate. One suitable device is the HIH-3610 series relative humidity sensor, by Honeywell Sensing and Control.

A person of ordinary skill in the art will appreciate that the first sensor 210 is not limited to sensing pressure, temperature, flow rate, oxygen content, humidity or combinations thereof. For example, carbon dioxide content, nitrogen content, resistance to fluid flow, magnetic charge and radiation (e.g., presence of nuclear isotope) are just some of the many fluid parameter measurements that may be sensed.

Figure 3:
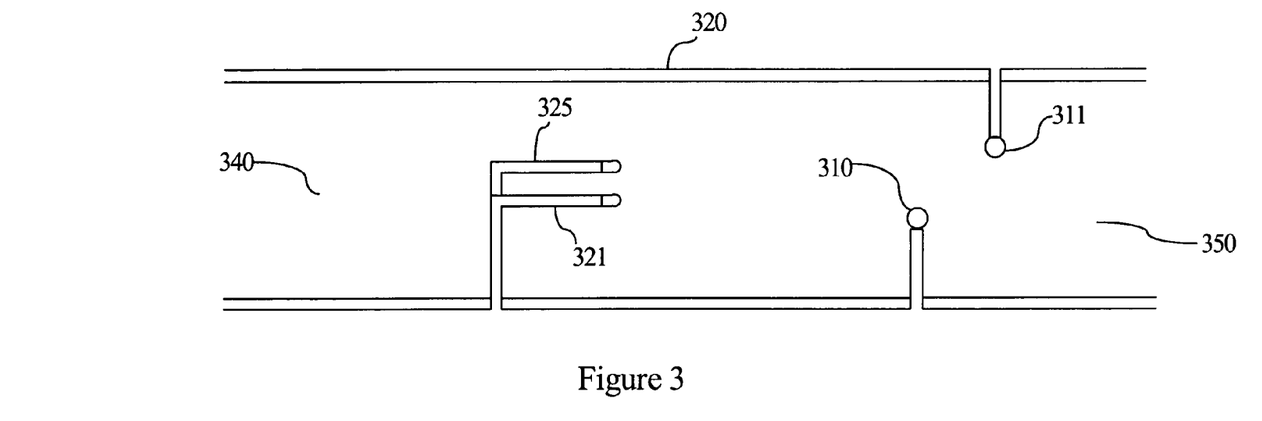
FIG. 3 is a side, cross-sectional view of a conduit, sensor and indicator in one embodiment of the invention.

FIG. 3 is a side, cross-sectional view of a conduit 320 and sensor 310 in one embodiment of the invention. FIG. 2 illustrates how the first sensor 210 may be located in substantial proximity to the proximal end 240 of the conduit 220. However, FIG. 3 illustrates how the first sensor 310 may be located near the distal end 350 of the conduit 320.

In response to the first sensor 310 detecting the parameter of the fluid, a first indicator 321, operatively coupled to the conduit 320 that transmits the fluid, may indicate whether a first predetermined condition is satisfied or not satisfied. For example, a predetermined condition may be that the fluid must be comprised of 80 percent oxygen. If the fluid comprises, for example, only 50 percent oxygen, the indicator 321 may be designed to indicate the predetermined condition is not satisfied. However, a person of ordinary skill in the art will appreciate that if the fluid comprises, for example, only 50 percent oxygen, the indicator 321 may be designed to indicate that a predetermined condition is satisfied because the predetermined condition may be that the fluid must be comprised of less than 80 percent oxygen.

In one embodiment of the invention, the indicator 321 comprises one or more light sources, such as one or more light emitting diodes (LEDs). In the present example, detection of only a 50 percent oxygen content may result in the LED indicator 321 being illuminated. The LED indicator 321 may then direct its light within or on to the conduit 320. The LED may be located within or outside the conduit. The LED may be a high intensity LED, such as the TLC.52 series by Vishay Semiconductors, which has a typical luminous intensity of 4000 millicandelas (mcd). The indicator 321, as stated above, may be comprised of multiple LEDs to, for example, increase the desired luminosity.

In addition, the conduit 320 may be constructed from a substantially translucent material. In other words, the material may transmit light imperfectly or perfectly so long as the LED light, shown inside or across the conduit 320, is transmitted through the walls of the conduit 320 to any observer. Thus, when a condition is or is not satisfied, depending on the designer's choice, the LED may illuminate some or all of the translucent conduit. Suitable materials for the conduit include silicone elastomers that meet USP Class VI and NSF-51 requirements and that are manufactured under strict Good Manufacturing Practices (GMP) in a controlled environment. The materials may be nonreactive to body tissues and fluids. One suitable material may be Silicon® Medical 2810073, by New Age Industries.

In another embodiment of the invention, the indicator 321 may be activated in response to a second parameter, such as humidity of the gas, that satisfies, or fails to satisfy, a preset condition or limit for the second parameter. This second parameter may be detected by a second sensor 311. For instance, a first LED 321 may illuminate if a certain level of oxygen, sensed by a first sensor 310, is not met. The same LED 321 may illuminate if a certain humidity, sensed by a second sensor 311, is not detected.

In an alternative embodiment of the invention, a second indicator 325 may be utilized. More precisely, in further response to the first sensor 310 detecting the parameter of the fluid, a second indicator 325, operatively coupled to the conduit 320, may indicate whether a first predetermined condition is satisfied. Thus, using the above example, if the fluid oxygen level is less than 80 percent, a second indicator such as a second LED 325, may illuminate. In addition, the second indicator may utilize multiple light sources.

In yet another embodiment of the invention, the second indicator 325, operatively coupled to the conduit and again in response to the first sensor detecting the parameter of the fluid, may indicate whether a second predetermined condition is satisfied. For example, the second LED 325 may illuminate if the fluid has 85% humidity, which is higher than a predetermined humidity level such as 70% humidity. Humidity may be sensed by a second sensor 311.

The above embodiments provide benefits in, for example, a medical setting because a patient or health care provider may quickly assess whether treatment regimens are being correctly carried out. In other words, a patient or subject may need to receive a breathing treatment in the middle of the night. Again, using the above example, a blue LED indicator(s) 321 may be programmed to activate if the fluid is comprised of more than 80 percent oxygen. A red LED indicator(s) 325 may be programmed to activate if the fluid is comprised of less than 80 percent oxygen. The clinician could tell from a distance if the breathing regiment was being followed because the conduit 320 may be illuminated with blue light. If the conduit 320 is illuminated with red light, the clinician could investigate the problem. The clinician could determine whether an issue existed without ever turning a light on in the patient's room.

As yet another illustration of utility, many patients that require breathing treatments may be elderly. That being the case, the patient may be farsighted. Thus, the patient may have difficulty reading LCD displays or mechanical pressure gauges. Such a patient could quickly ascertain whether he is receiving, for example, the proper level of oxygen, by ensuring the conduit 320 is glowing blue and not red.

Figure 4:
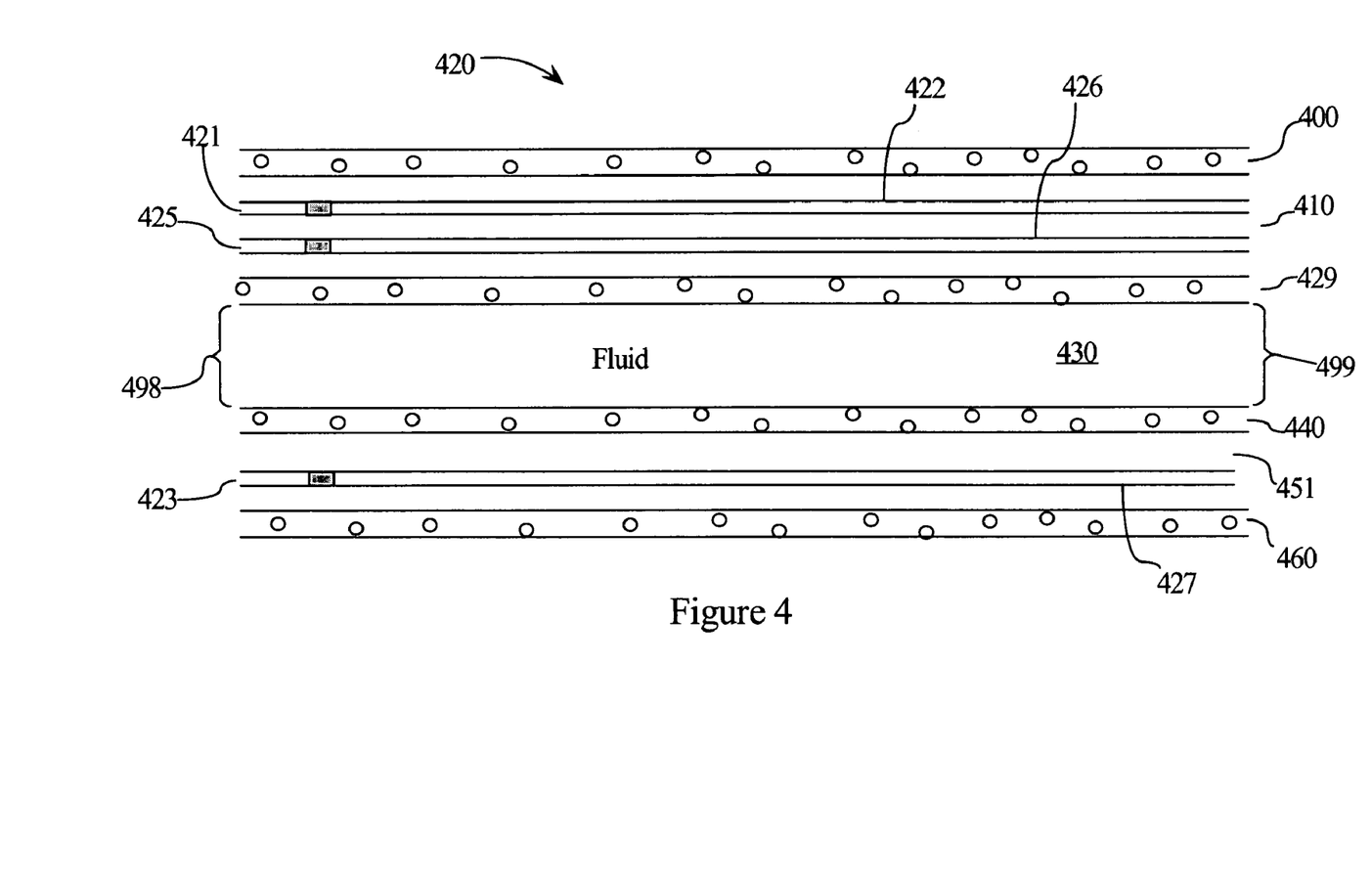
FIG. 4 is a side, cross-sectional view of a conduit in one embodiment of the invention.

FIG. 4 illustrates an alternative embodiment of the invention. The conduit 420 has a channel 430 for transmitting fluid. The channel 430 is separated from another channel 410 by a wall 429. The channel 410 may be used for an alternative form of indicator such as a fiber optic light source. The fiber optic cable 422 may be constructed from plastic, having a core of approximately 0.04 inches or 1 mm diameter. The optic cable 422 may transmit visible red light (wavelength=650 nm) from an LED 421. A second indicator may be comprised of a second LED 425 and second optic cable 426. Yet another LED 423 and optic cable 427 may reside in another channel 451 that is separated from the fluid transmitting channel 430 by a wall 440. Use of fiber optics, for example, may be said to locate the light source or light path between the conduit input 498 and conduit output 499. The fiber optic cable itself 427 is a source of light for the conduit. A person of ordinary skill in the art will appreciate that a separate channel, for example, is not necessary for the fiber optic cable 422. Such a cable 422 may reside in the fluid channel 430.

Figure 9:
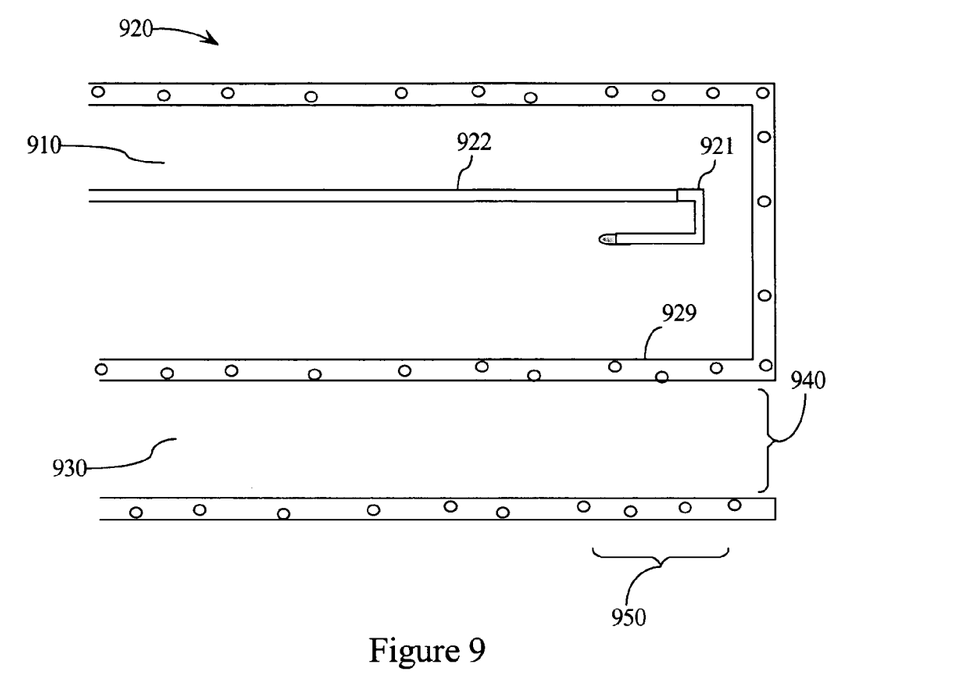
FIG. 9 is a side, cross-sectional view of a conduit in one embodiment of the invention.

FIG. 9 illustrates an additional embodiment of the invention. Conduit 920 has a channel 930 for transmitting fluid. The channel 930 is separated from another channel 910 by a wall 929. The channel 910 may be used to carry wiring 922 to an LED indicator, such as a first indicator 921, that may be located in substantial proximity to the distal end 950 of the conduit 920, near the conduit output 940.

Figure 11:
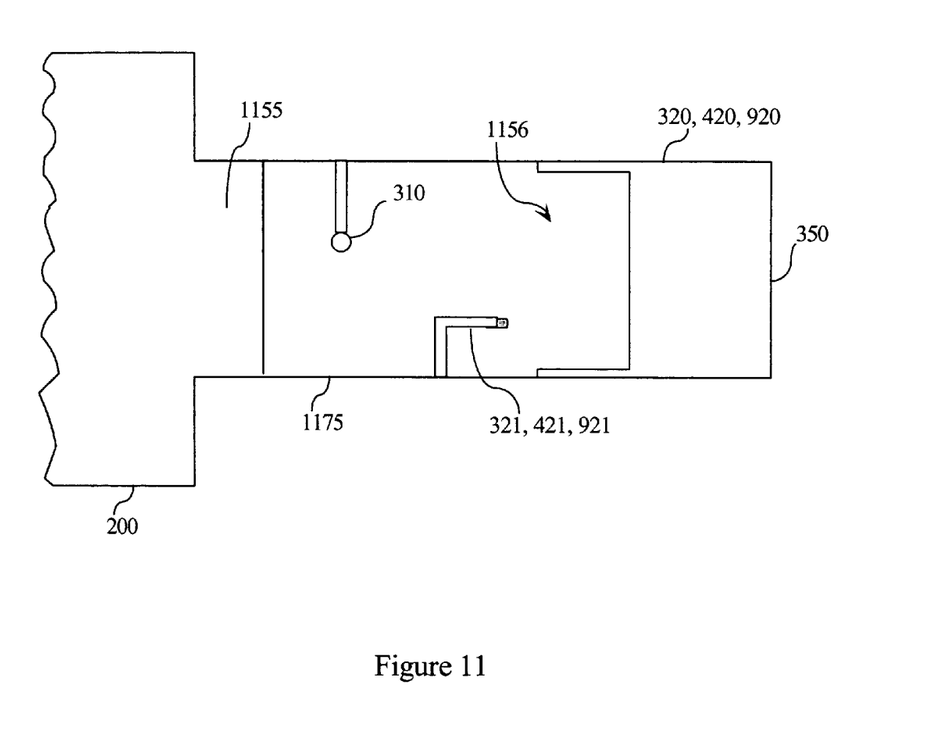
FIG. 11 is a side, cross-sectional view of a conduit, fluid source and fluid indicator device in one embodiment of the invention.

FIG. 11 describes an embodiment of the invention with a fluid indicator device 1175 that is operatively coupled between a fluid source 200 and a conduit 320, 420, 920. For example, the conduit 320, 420, 920 may fit snugly over a neck or protrusion 1156 of the fluid indicator device 1175. A sensor 310 may be mounted to the fluid indicator device 1175. The sensor 310 may detect a first parameter of the fluid such as oxygen content. A first indicator, such as a LED 321, 421, 921 may also be mounted to the fluid indicator device 1175. In response to the sensor 310 detecting the oxygen content of the fluid, the LED 321, 421, 921 may illuminate provided, for example, the oxygen content is too low. By doing so, the LED 321, 421, 921 may project light into the conduit thus illuminating a portion of the conduit 320, 420, 920. Those of ordinary skill in the art will appreciate that the fluid indicator device 1175 need not be placed in between the fluid source 200 and conduit 320, 420, 920. For example, the fluid indicator device 1175 may be placed at the conduit output 350, or within, or substantially within, the conduit 320, 420, 920 or the output 1155 of the fluid source 200.

Still another alternative embodiment of the invention is now described. As described before, a fluid source is operatively coupled to a conduit. Again referring to FIG. 4, the conduit 420 may have a channel 410 for an indicator such as an LED 421 and fiber optic cable 422. If the conduit 420 were to be crimped or kinked, the fiber optic cable would stop transmitting light at the sight of the kink. Thus, the indicator 421, 422 would indicate a resistance to fluid flow within the conduit 420 due to the kink.

Figure 6:
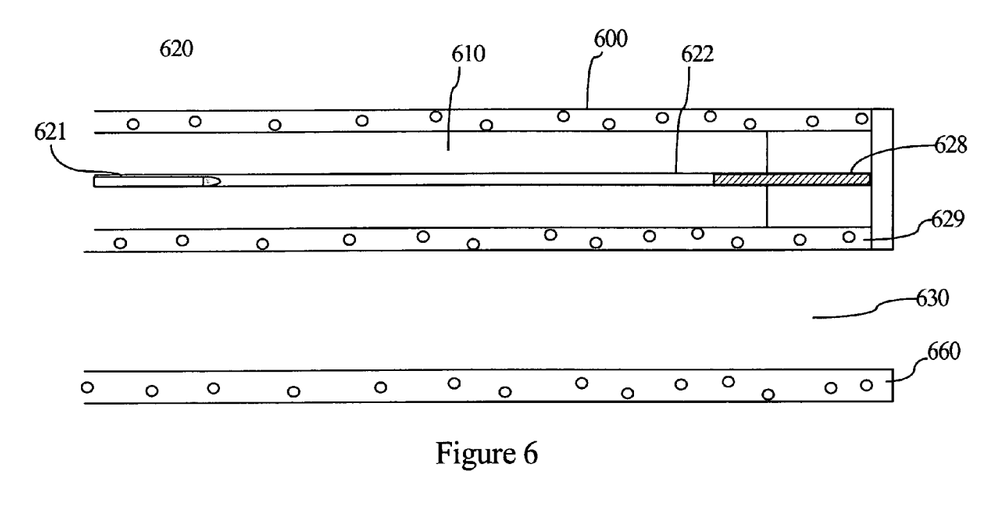
FIG. 6 is a side, cross-sectional view of a conduit in one embodiment of the invention.

FIG. 6 describes yet another embodiment of the invention wherein a fluid source (not shown) is operatively coupled to a conduit 620 that has a channel 630 for transmitting fluid. The conduit 620 may have another channel 610 comprising a transmitter 621 and fiber optic cable 622. The invention may also comprise a fiber optic relay system comprising an optical receiver 628. The receiver 628, upon receiving light from the transmitter 621, may deem such a receipt as a predetermined condition being satisfied. However, should a kink be placed in the conduit 620, thus causing a resistance to fluid flow, the receiver 628 would no longer receive light from the transmitter 621. Upon such a condition, the receiver 628 may signal to a data processing system that the conduit 620 flow path has likely been compromised. An audio alarm may then be sounded.

Figure 5:
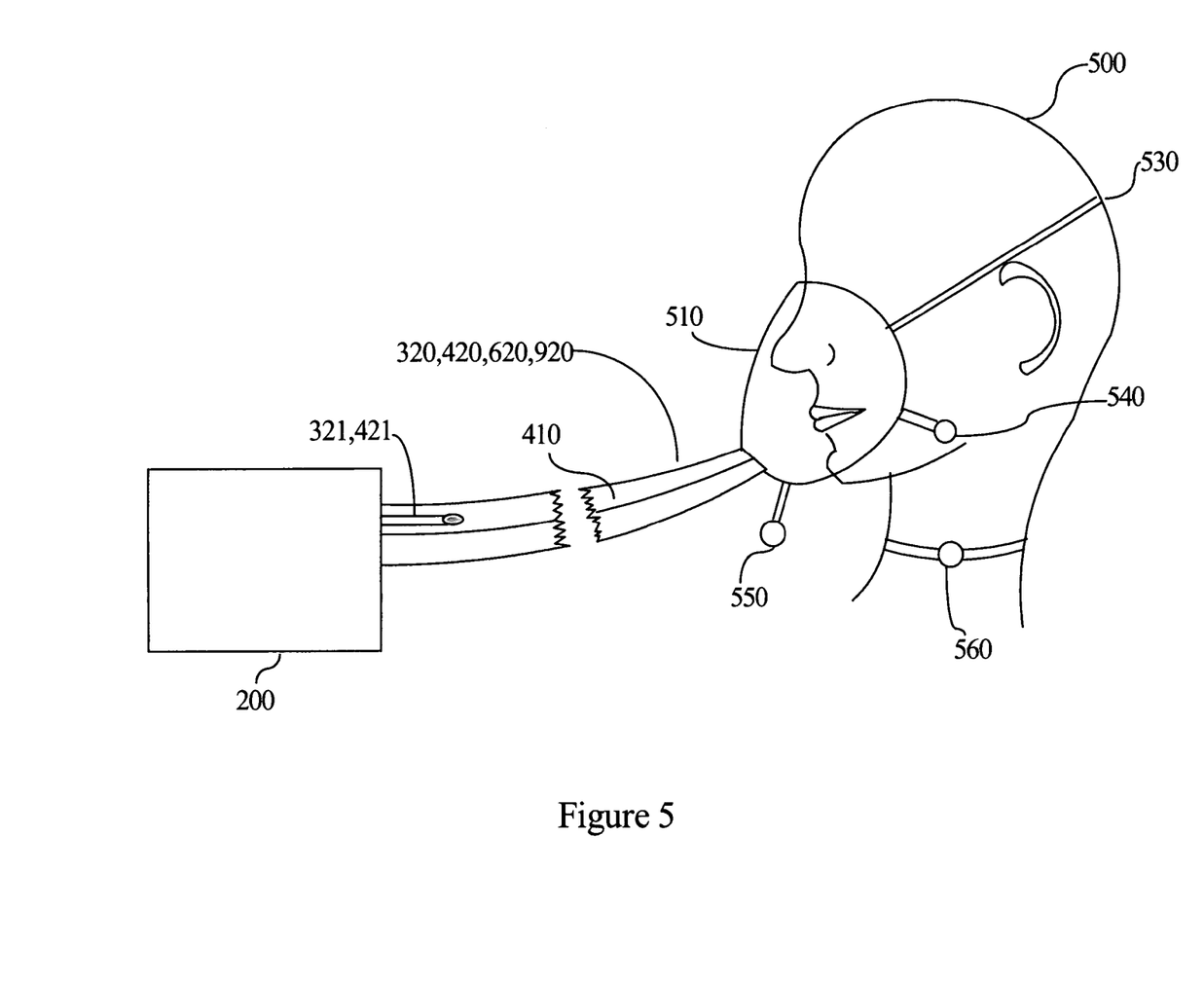
FIG. 5 is a side view of a conduit, gas mask and plurality of sensors in one embodiment of the invention.

FIG. 5 illustrates another embodiment of the invention. A conduit 320, 420, 620, 920 connects to a gas mask 510 which is affixed to the head of a patient 500 by an elastic strip 530. A second sensor 540 detects the proximity of the conduit output to a patient's body. The second sensor 540 may comprise a thermistor which detects heat from the patient's body. The thermistor signal may be transmitted, using circuitry extending through a channel 410 in the conduit 320, 420, 620, 920 to an indicator such as the LED 321, 421. Thus, if the second sensor 540 detects that a first predetermined condition, such as certain temperature from the patient's body heat, is satisfied, the indicator 321, 421 may illuminate. Thus, a health care practitioner could quickly determine, without turning lights on in a patient's room, if the gas mask 510, and thus the conduit 320, 420, 620, 920, was still in proximity to the patient 500. This helps address problems whereby a patient may unconsciously remove the breathing mask during his or her sleep.

Another embodiment of the invention illustrates an alternative method for detecting proximity of the conduit 320, 420, 620, 920 to the patient 500. Another sensor 560 may incorporate technology such as a radiofrequency identification system (RFID). The RFID 560 basically comprises a disposable electronic circuit and antenna. As those of ordinary skill in the art will appreciate, the RFID 560 is coupled to a transmitter antenna 550, which may be located near the mask 510 and conduit 320, 420, 620, 920. The transmitter antenna 550 may subject the RFID 560 to a specific frequency, provided the RFID 560 is in proximity to the transmitter 550. The response from the RFID 560 is then picked up by the receiver antenna 550. If the RFID response matches a characteristic frequency, the determination may be made by a data processing system that the first indicator 321, 421 may be illuminated. Those of ordinary skill in the art will recognize that, for example, the storage of information in an RFID, as well as the reading of that information, is well known in the art. Furthermore, a person of ordinary skill in the art will recognize that the RFID 560 may be a passive tag that has no power source. The RFID 560 may also be an "active" tag that uses a battery. RFID systems use frequencies in the kilohertz, megahertz and gigahertz ranges. Frequency sweep techniques, known to those of ordinary skill in the art, may be incorporated to handle different RFID frequencies.

Figure 8:
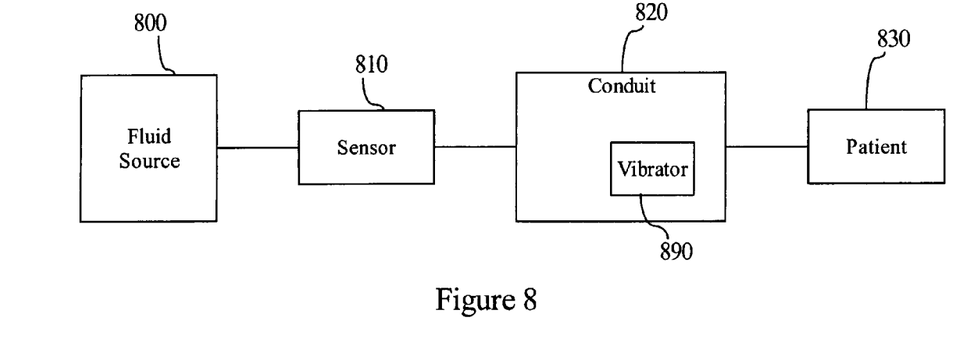
FIG. 8 is a block diagram of a conduit and vibrator in one embodiment of the invention.

FIG. 8 describes an embodiment of the invention wherein a fluid source 800 is operatively coupled to a conduit 820. A first sensor 810 detects a first parameter of the fluid, the first sensor 810 being in operative communication with the fluid. In response to the first sensor 810 detecting the first parameter of the fluid, a first indicator 890 indicates whether the first parameter fails to satisfy a first predetermined condition, wherein the first indicator 890 is operatively coupled to the conduit. The indicator 890 comprises a vibrator mechanism that transmits vibrations to the conduit 820 when the first parameter fails to satisfy a first predetermined condition. For example, if the predetermined condition requires at least 80 percent oxygen content in the fluid, the vibrator may begin vibrating if a 50 percent oxygen content is detected. The vibrations are transmitted through the conduit to the patient. Thus, a sleeping patient may be alerted to a failure, or satisfaction, of a condition in the system. A person of ordinary skill in the art will appreciate that such vibrating mechanisms are readily available. One suitable device may be the 4AL-01WA vibration motor by JinLong Machinery. Furthermore, the vibrating mechanism may have a "soft start" whereby the intensity of vibrations ramp from low intensity to high intensity over a period of time.

A person or ordinary skill in the art will further appreciate that any of the aforementioned indicators need not comprise or be limited to visual indicators. Any such indicator may include an auditory alarm that may be sounded when a predetermined condition, such as inadequate oxygen content, is detected.

In addition, a person of ordinary skill in the art will realize the invention's utility is not limited to the specific embodiments described herein. For example, instead of transmitting a therapeutic gas, such as oxygen, to a patient, the conduit fluid channel 630 may transmit a fluid in the liquid state, such as a medication in an intravenous (IV) drip system. Blood, with both liquid and solid components, may also be transmitted though the conduit fluid channel 630. Furthermore, a filter, such as an ultraviolet radiation filter, may be incorporated at any contact point with the fluid to act as an antimicrobial agent. For example, in FIG. 2 the filter 241 may be located between the fluid supply 200 and conduit 220. There are many industrial applications as well. For example, gasoline or other fluids may be transmitted using the invention. For especially long transmissions (e.g., more than 0.5 miles or 1 km) using fiber optics as an indicator, a laser may be substituted for the LED light source. Furthermore, optical regenerators may be used to combat signal degradation.

Figure 10:
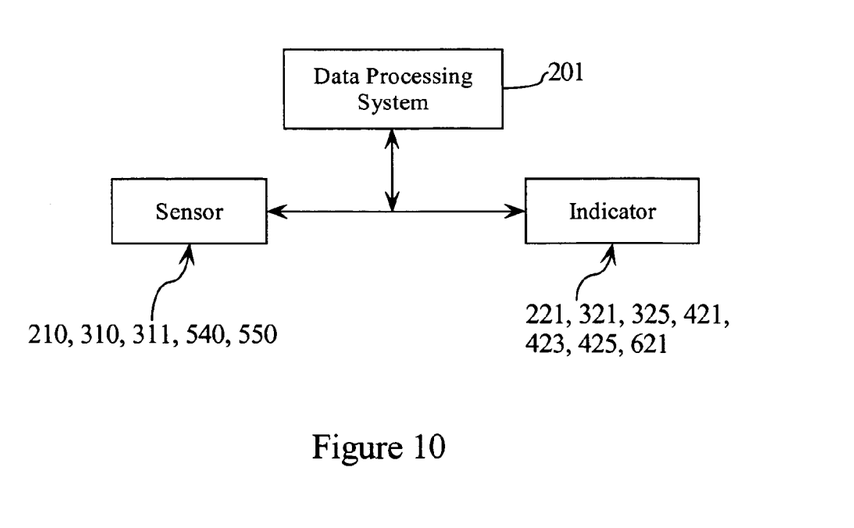
FIG. 10 is a block diagram of a data processing system, sensor and indicator.

Referring to FIG. 10, as a person of ordinary skill in the art will appreciate, any of the aforementioned sensors 210, 310, 311, 540, 550 or indicators 221, 321, 325, 421, 423, 425, 621 may communicate with one or more computer program products and a data processing system 201. For example, a sensor, such as a flow meter, may be coupled to a data processing system 201 to calculate a flow rate. The data processing system 201 may then, using logic circuitry and/or one or more computer program products, compare the calculated flow rate to a predetermined flow rate. Based on the comparison, a signal may be transmitted to the indicator 221, 321, 325, 421, 423, 425, 621 instructing the indicator to illuminate. A person of ordinary skill in the art will further appreciate that the sensor 210, 310, 311, 540, 550 may communicate with the indicator 221, 321, 325, 421, 423, 425, 621 without use of a separate data processing system 201.

Figure 7:
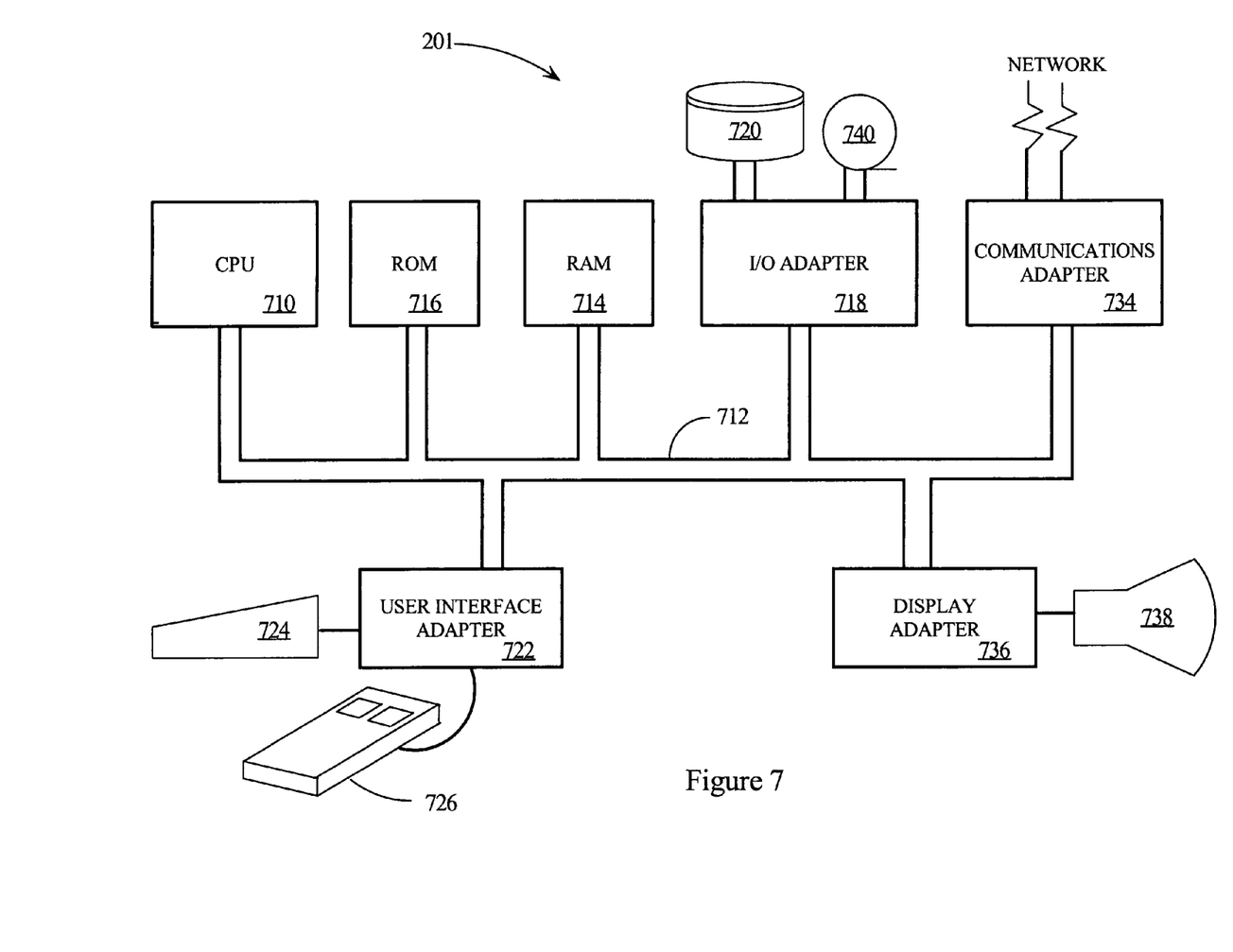
FIG. 7 is a block diagram of a data processing system in one embodiment of the invention.

Referring to FIG. 7, an example is shown of a data processing system 201, which may be used for implementing any of the aforementioned embodiments of the invention. The system has a central processing unit (CPU) 710, which is coupled to various other components by system bus 712. Read only memory ("ROM") 716 is coupled to the system bus 712 and includes a basic input/output system ("BIOS") that controls certain basic functions of the data processing system 201. Random access memory ("RAM") 714, I/O adapter 718, and communications adapter 734 are also coupled to the system bus 712. I/O adapter 718 may be a small computer system interface ("SCSI") adapter that communicates with a disk storage device 720. Communications adapter 734 interconnects bus 712 with an outside network enabling the data processing system 201 to communicate with other such systems. Input/Output devices are also connected to system bus 712 via user interface adapter 722 and display adapter 736. Keyboard 724 and mouse 726 are interconnected to bus 712 via user interface adapter 722. Display adapter 736 connects display monitor 738 to system bus 712. In this manner, a user is capable of inputting to the system throughout the keyboard 724 or mouse 726 and receiving output from the system via display 738.

It will be understood that certain of the above-described structures, functions and operations of the above-described embodiments are not necessary to practice the present invention and are included in the description simply for completeness of an example embodiment or embodiments. It is therefore to be understood that within the scope of the claims, the invention may be practiced otherwise than as specifically described without actually departing from the spirit and scope of the present invention. Finally, all patents, publications and standards referenced herein are hereby incorporated by reference.

What is claimed is:

1. A system comprising:
   a fluid source;
   a conduit having an input and an output, the conduit input being operatively coupled to the fluid source so that a fluid from the fluid source may be transmitted from the fluid source to the conduit output;
   a first sensor for detecting a first parameter of the fluid, the first sensor being in operative communication with the fluid;
   a first indicator comprising one or more light sources; and
   in response to the first sensor detecting the first parameter of the fluid, the first indicator indicating whether the first parameter fails to satisfy a first predetermined condition by illuminating at least a portion of the conduit, wherein the first indicator is operatively coupled to the conduit.

2. The system of claim 1, wherein the one or more light sources are located substantially between the conduit input and conduit output.

3. The system of claim 1, wherein the one or more light sources are located in substantial proximity to the conduit output.

4. The system of claim 1, wherein the one or more light sources comprise one or more LEDs.

5. The system of claim 1, wherein the one or more light sources comprise one or more fiber optic cables.

6. The system of claim 1, wherein the conduit is substantially comprised of a substantially translucent material.

7. The system of claim 1, wherein the first predetermined condition is a concentration level of a oxygen within the fluid.

8. The system of claim 1 further comprising a second indicator, operatively coupled to the conduit, for indicating, in response to the first sensor detecting the first parameter of the fluid, whether the first parameter satisfies the first predetermined condition.

9. The system of claim 1, wherein the first indicator is located substantially within the conduit.

10. The system of claim 1 further comprising:
   a second sensor for detecting a second parameter of the fluid, the second sensor being in operative communication with the fluid; and
   in response to the second sensor detecting the second parameter of the fluid, a second indicator indicating whether the second parameter fails to satisfy a second predetermined condition, wherein the second indicator is operatively coupled to the conduit.

11. The system of claim 1 further comprising:
   a second sensor for detecting a second parameter of the fluid, the second sensor being in operative communication with the fluid; and
   in response to the second sensor detecting the second parameter of the fluid, the first indicator indicating whether the second parameter fails to satisfy a second predetermined condition, wherein the second indicator is operatively coupled to the conduit.

12. The system of claim 1, wherein the fluid is in a gaseous state.

13. The system of claim 1 further comprising a second sensor, the second sensor detecting the proximity of a portion of the conduit to a patient's body.

14. The system of claim 1 further comprising a radiation source for radiating the fluid, wherein the radiation source is in communication with the fluid.

15. A method comprising the steps of:
   receiving a fluid from a fluid source using a conduit having an input and an output, the conduit input being operatively coupled to the fluid source so that the fluid may be transmitted from the fluid source to the conduit output;
   detecting a first parameter of the fluid using a first sensor, the first sensor being in operative communication with the fluid; and
   in response to the first sensor detecting the first parameter of the fluid, indicating, using a first indicator that is operatively coupled to the conduit, whether the first parameter fails to satisfy a first predetermined condition by illuminating at least a portion of the conduit.

16. The method of claim 15, further comprising the step of, in response to the first sensor detecting the first parameter of the fluid, using a second indicator, comprising a vibrating means and that is operatively coupled to the conduit, to indicate whether the first parameter fails to satisfy the first predetermined condition by vibrating a least a portion of the conduit.

17. The method of claim 15, further comprising the step of, in response to a second sensor detecting a second parameter of the fluid, using a second indicator, comprising a vibrating means and that is operatively coupled to the conduit, to indicate whether the second parameter fails to satisfy a second predetermined condition by vibrating a least a portion of the conduit.

18. The method of claim 15, wherein the first parameter of the fluid is resistance to fluid flow within the conduit.

19. The method of claim 15, further comprising the step of, in response to the first sensor detecting the first parameter of the fluid, using a second indicator that is operatively coupled to the conduit to indicate whether the first parameter satisfies the first predetermined condition by illuminating a least a portion of the conduit.

20. A fluid indicator device for operatively coupling to a fluid source and a conduit, the conduit being operable to transmit a fluid from the fluid source to an output of the conduit, the fluid indicator device comprising:
   a first sensor for operatively communicating with the fluid and for detecting a first parameter of the fluid,
   a first indicator, comprising one or more light sources, for operatively coupling to the conduit; and
   in response to the first sensor detecting the first parameter of the fluid, the first indicator being operable to indicate whether the first parameter fails to satisfy a first predetermined condition by illuminating at least a portion of the conduit.

* * * * *